United States Patent [19]

Scott

[11] 4,402,308

[45] Sep. 6, 1983

[54] MEDICAL IMPLANTATION DEVICE

[76] Inventor: Walter P. Scott, 314 Ponte Vedra Blvd., Ponte Vedra, Fla. 32082

[21] Appl. No.: 203,320

[22] Filed: Nov. 3, 1980

[51] Int. Cl.³ .............................................. A61N 5/00
[52] U.S. Cl. ........................................ 128/1.2; 604/60
[58] Field of Search ................. 128/216, 217, 264, 1.2, 128/654; 604/60

[56] References Cited

U.S. PATENT DOCUMENTS

| | | | |
|---|---|---|---|
| 2,269,963 | 1/1942 | Wappler | 128/297 |
| 2,761,446 | 9/1956 | Reed | 128/217 |
| 3,155,093 | 11/1964 | Enström et al. | 128/216 |
| 3,921,632 | 11/1975 | Bardani | 128/217 |
| 4,086,914 | 5/1978 | Moore | 128/1.2 |
| 4,167,179 | 11/1979 | Kirsch | 128/1.2 |

OTHER PUBLICATIONS

Radiology, vol. 122, No. 3, Mar. 1977, pp. 832-834, Walter P. Scott.
The American Journal Roentgenology, Radium Therapy, and Nuclear Medicine, vol. CXIV, No. 3, Mar. 1972, pp. 620-622, W. P. Scott, M.D.
Radiology, vol. 105, No. 2, Nov. 1972, pp. 454-455, Walter P. Scott, M.D.
Radiology, vol. 117, No. 3, Dec. 1975, pp. 734-735, Walter P. Scott, M.D.
Surgery, Gynecology & Obstetrics, vol. 142, May 1976, pp. 667-670, W. P. Scott.

Primary Examiner—George F. Lesmes
Assistant Examiner—Nancy A. B. Swisher
Attorney, Agent, or Firm—Arthur G. Yeager

[57] ABSTRACT

An injector for implanting materials comprising a hollow tubular sheath with a sharpened point suitable for injecting into human tissue and a slotted needle slidably and rotatably mounted inside said sheath, the sheath being retractable to expose any portion or all of the slotted needle, and the needle being rotatable within the sheath. This device is employed for implanting radioactive seeds in human tissue for treatment thereof.

31 Claims, 12 Drawing Figures

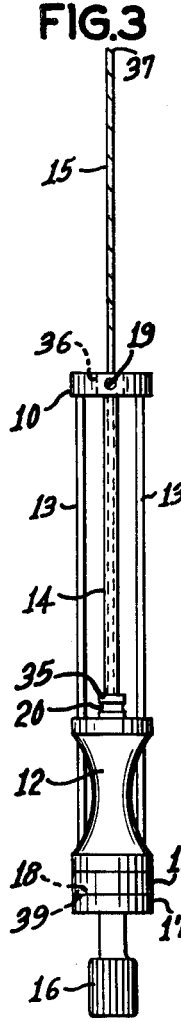
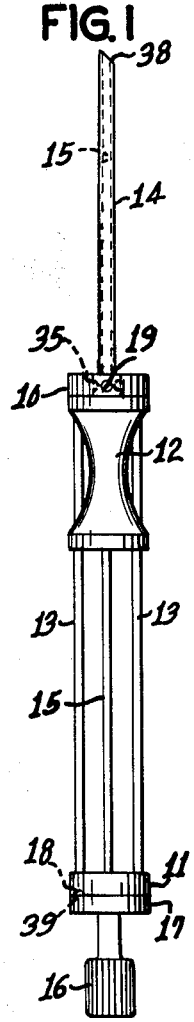
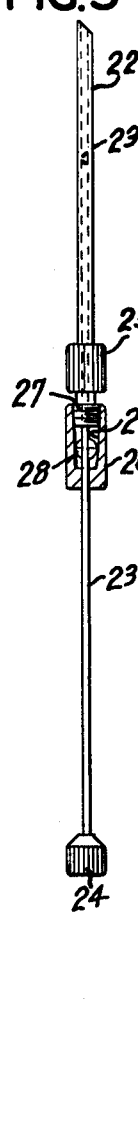
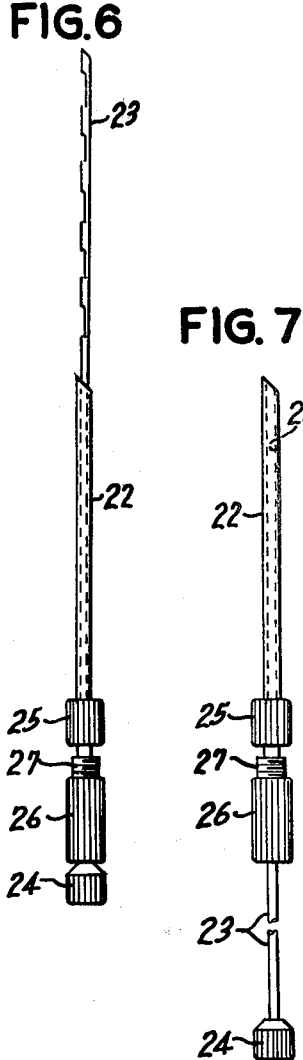
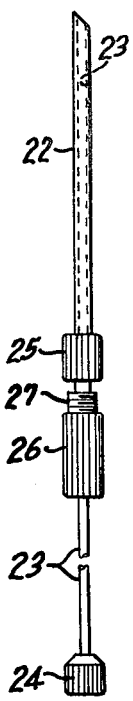
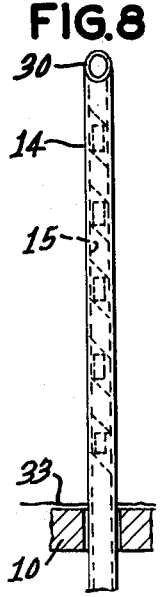
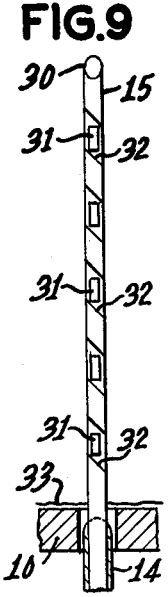
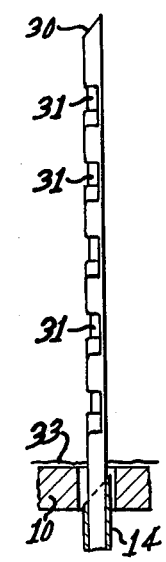
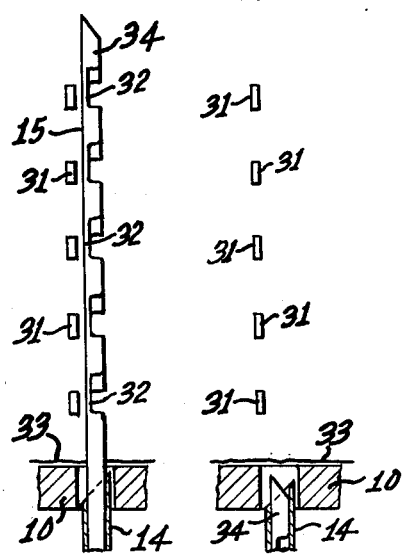
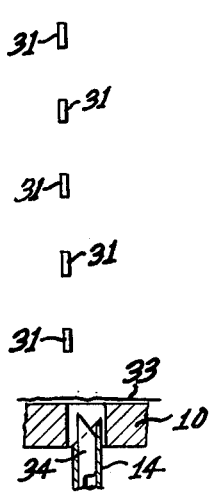

MEDICAL IMPLANTATION DEVICE

BACKGROUND OF THE INVENTION

For many years it has been a common medical-surgical technique in the treatment of malignant tumors to inject radioactive seeds in the tumor that will provide radiation from the seeds. These seeds are small tubular sections filled with a radioactive material and sealed at each end. These seeds may be of any convenient size although they are frequently not more than one millimeter in diameter and 3–4 millimeters in length. The number and positioning of the seeds in the tissue depends upon the treatment considered most appropriate by the physician.

The devices for accomplishing these implantation treatments have varied considerably. One type which was used in the first of such treatments is shown in U.S. Pat. No. 2,269,963 having the appearance of a hand gun with a plunger along the barrel of the gun to advance and deposit seeds from the forward end of the device. Other more recent devices are seen in U.S. Pat. Nos. 3,921,632; 4,086,914; and 4,167,179.

These techniques involving guns or needles for implanting such seeds have proved to be deficient in many respects, particularly because they do not provide a means for implanting seeds at a precise spacing and location to perform the desired treatment. These deficiencies led me to seek other devices and methods by which the seeds could be located in a fixed spaced relationship to each other. One method I developed involved the use of a suture containing the seeds in a fixed spaced relationship. After the suture was threaded into the tissue the suture would be absorbed naturally in the human body, leaving the seeds in a fixed spaced relationship. The same basic idea was employed using a needle to inject seeds separated by absorbable spacers. My techniques were reported in the following articles:

The American Journal Roentgenology, Radium Therapy, And Nuclear Medicine, Vol. CXIV, No. 3 March, 1972, Pages 620-622.
Radiology Vol. 105, No. 2, November 1972, Pages 454-455
Radiology Vol. 117, No. 3, December 1975, Pages 734-735
Surgery, Gynecology & Obstetrics, Vol. 1 or 2 May, 1976, Pages 667-670.

A more recent development of mine is a sheathed needle injection device which is loaded with 1–5 seeds without any absorbable spacer material, the sheathed needle is injected into the tissue, the seeds are ejected from the needle through slots in the sheath, and the sheathed needle is then withdrawn leaving the seeds in the tissue. This technique is described in Radiology, Vol. 122, No. 3, March 1977, Pages 832, 834. While this reported device is a vast improvement over previous techniques it, also lacked some precision in positioning the seeds because the method of ejecting seeds from the needle functioned imperfectly. Accordingly I have developed the device of this invention as a new and improved injector for implanting radioactive seeds in human tissue with precision.

BRIEF DESCRIPTION OF THE INVENTION

This invention provides an injector for implanting materials comprising an elongated needle having a forward end portion and a rearward end portion, including transverse slots spaced therealong to receive materials to be implanted within a body, means attached to said rearward end portion to rotate said needle radially about its longitudinal axis; and an elongated continuous sheath having a forward open end and slidably mounted on and surrounding said needle over a length at least sufficient to cover all of said slots, means for retracting said sheath to expose said slots on said forward end portion of said needle. In one embodiment of this invention the injector comprises a housing upon which the sheath is mounted to extend beyond the housing or be retracted within the housing while the needle is slidable lengthwise and rotatable radially within said sheath. In another embodiment of this invention the sheath is fitted at its rearward end with a threaded portion and a clamping device to cooperate with a finger grip portion sliding over the needle to clamp the needle in any desired position relative to the sheath.

BRIEF DESCRIPTION OF THE DRAWINGS

The novel features believed to be characteristic of this invention are set forth with particularity in the appended claims. The invention, itself, however, both as to its organization and method of operation, together with further objects and advantages thereof, may best be understood by reference to the following description taken in connection with the accompanying drawings in which:

FIG. 1 is a top plan view of one of the injectors of this invention.

FIG. 2 is a end elevational view of the injector shown in FIG. 1.

FIG. 3 is a plan view similar to that of FIG. 1 except that the sheath has been retracted from the needle.

FIG. 4 is a view similar to that of FIG. 3 except that the needle has been retracted.

FIG. 5 is a top plan view of an alternate injector of this invention.

FIG. 6 is a view similar to that of FIG. 5 except that the sheath has been retracted.

FIG. 7 is a view similar to that of FIG. 6 except that the needle has been retracted.

FIG. 8 is an enlarged partial view of the needle containing seeds and covered with the sheath.

FIG. 9 is an enlarged view similar to that of FIG. 8 except that the sheath has been retracted.

FIG. 10 is a side view of the portion shown in FIG. 9.

FIG. 11 is a view similar to that of FIG. 10 except that the needle has been rotated 180°.

FIG. 12 is a view showing the implanted seeds after retraction of the needle from the view shown in FIG. 11.

DETAILED DESCRIPTION OF THE INVENTION

In the attached drawings there are shown two embodiments of this invention, one of which is incorporated in FIGS. 1–4 and the other of which is incorporated in FIGS. 5–7. The enlarged views of FIGS. 8–12 apply equally to both of the devices described above.

With respect to the embodiment of FIGS. 1–4 there is a housing comprised of forward stop plate 10, rearward stop plate 11, and two guide rods 13. This combination forms a fixed rigid structure upon which the remainder of the device is mounted and moves. Tubular sheath 14 is fixed to finger grip 12, which, in turn, is mounted on guide rods 13 sliding with linear movement between stop plates 10 and 11. It may be seen that sheath 14 can be moved from a maximum extension as shown in FIG. 1 to a maximum retraction as shown in FIG. 4, or it may be positioned at any place in between these two extremes. Mounted inside of sheath 14 in a slidable and rotatable fashion is needle 15 which is one continuous rod from its tip 37 through the interior of sheath 14 to transverse plate 17 which is rigidly fixed to control knob 16. This may best be seen in FIG. 4 where needle 15 has been retracted only to the extent of the full retraction of sheath 14, but nothing prevents the operator from retracting needle 15 still farther, even completely separating it from the housing and from sheath 14.

Plate 17 contains a small index knob 18 which cooperates with index knob seat 39 in stop plate 11 to provide a positive index to identify the alignment of needle 15 and sheath 14 for injection into the body. This is helpful to the operator to be sure the angular tip 37 of needle 15 is turned at the same angle as tip 38 of sheath 14 to form a substantially closed and sharpened end for insertion into the body.

When needle 15 and sheath 14 are both extended in the position shown in FIG. 1 they are ready for insertion into the tissue in which the materials are to be implanted. In order to provide some stability for this position there is provided a projection 35 into which has been machined a circular groove 20. When finger grip 12 is in the forward position as shown in FIG. 1 projection 35 slides into hole 36 in forward stop plate 10 and groove 20 is engaged by one or more spring loaded ball detents 19. In this fashion finger grip 12 is snap-locked into forward stop plate 10. Needle 15 is of such a length that when plate 17 is pressed against rearward stop plate 11, the tips 37 and 38 are in the same plane.

Tip 37 of needle 15 and the tip 38 of sheath 14 are both tapered to produce a sharpened point needed for easy injection into the body tissue and these two tapered tips are matched to produce a single smooth surface when finger knob 16 is rotated in such a fashion that index knob 18 is inserted into index knob seat 39. The seating of knob 18 into seat 39 can be accomplished by feel as well as by eye.

In an alternative embodiment of this invention there is shown the device of FIGS. 5–7. A hollow tubular sheath 22 is terminated at its rearward end by finger grip 25. Needle 23 is mounted inside of sheath 22 in a slidable and rotatable fashion. To the rearward end of needle 23 is rigidly affixed finger grip 24. Mounted in a slidable fashion over needle 23 is a housing in the form of a clamp grip 26 which cooperates with finger grip 25 to clamp sheath 22 in any desired position with respect to needle 23. At the rear portion of finger grip 25 there is a male threaded portion 27 and a clamping means 28 to clamp around needle 23 when it is desired to do so. In this drawing the clamping means is a bifurcated hollow ball 28 through which needle 23 passes and which is clamped upon needle 23 when clamp grip 26 having an internal female threaded portion is screwed onto threaded portion 27 causing ball 28 to be squeezed tightly around needle 23 by the action of tapered bore 29 in finger grip 26.

In FIG. 6 sheath 22 is shown retracted and in FIG. 7 needle 23 is shown to be retracted into sheath 22 and can be retracted even farther and be completely separated from sheath 22 and from finger grip 26. In neither of these drawings is the clamping device of FIG. 5 engaged and so there is a freedom of movement between sheath 22 and needle 23. The device of FIGS. 5–7 is particularly useful when it is desired to implant less than the total number of seeds capable of being handled by this device. Finger grip 26 may be clamped to sheath 22 and needle 23 at any desired location, e.g. for the implantation of 2 or 3 seeds rather than 5.

Each of the elongated sheaths 14 and 22 in both embodiments, as herein shown and described, is seen to be continuous with openings only at its opposite ends, i.e. the cylindrical wall of each sheath is uninterrupted throughout its length. Also each of the sheaths 14 and 22 are slidingly disposed on and juxtaposed about the respective needles 15 and 23 so that the sheaths provide protective covers for all of the slots in the needles and when the sheaths are slidingly fully retracted on the needles, the entire circumference of the needle and slots, as well as any implantable materials in the slots, are uncovered and exposed for implantation of such materials upon rotation of the needle at least 180° whereby the unslotted side of the needles are adjacent the implanted materials, as seen in FIG. 11.

In both of the embodiments described above with respect to FIGS. 1–7 the interior needle device is the same and can best be seen in detail in FIGS. 8–12. Needle 15 is machined in a transverse direction to produce a series of slots 32 spaced along the length of the forward portion of needle 15. These slots 32 are of sufficient size for each to contain a single implant material, preferably a radioactive seed which has the form of a short cylindrical section of very small diameter and of a length about 3–5 times its diameter. In the preferred injector needle 15 is approximately 1 millimeter in diameter and the forward portion which extends from stop plate 10 to the tip is approximately 5–6 centimeters in length. Since a convenient spacing for radioactive seeds in many instances is 1 centimeter, each of slots 32 is approximately 0.5 centimeter from its center to the center of the next adjacent slot 32. There may, of course be occasions for other spacings between seeds or other sizes of seeds, and this invention is intended to include such alternatives. This arrangement provides a needle that is capable of implanting five seeds at one time. It is a preferred feature of this invention that slots 32 are cut such that their end portions are disposed at an angle to the lengthwise axis of needle 15. Preferably this angle is approximately 45° although other angles are also operable. The angular arrangement is made so that the seeds may be easily and precisely ejected from the needle 15 and left in the tissue in which they are to be implanted by a screw action when the needle is rotated prior to retraction. As described earlier the tip of needle 15 is sharpened by a bevel 30 which corresponds exactly to a similar bevel or sheath 14. When needle 15, seeds 31, and sheath 14 are injected into tissue 33 as shown in FIG. 8 and the sheath 14 is retracted as shown in FIG. 10, needle 15 is rotated clockwise at least 180° to the position shown at 34 in FIG. 11. This rotation of needle 15 causes the tissue to sweep seeds 31 out of slots 32 by reason of the angular edges of slots 32. It is preferable that the edges of slots 32 be rounded to eliminate sharp corners that might tear the surrounding tissue or cause the implanted seeds 31 to become dislodged from their precise spacing when needle 15 is rotated and retracted. Needle 15 in the position shown at 34 can then be retracted into sheath 14 without fear of moving seeds 31 from their desired positioning. Accordingly when needle 34 is retracted into sheath 14 it will be in the position shown in FIG. 12 leaving the five seeds 31 in the desired position. It has been found to be advantageous to actually twirl needle 15 one or more complete 360° turns before stopping in the position shown in FIG. 11 and retracting the needle as in FIG. 12.

Another embodiment of this invention is to employ with any of the described injectors a needle 15 which is made of material that is absorbable by the natural functioning of the body in the same fashion as the absorbable spacers and sutures of the prior art mentioned above. In this embodiment a slotted needle made of absorbable material, e.g. polyglactin, is loaded with seeds, inserted into a sheath 14, and inserted into a body. Sheath 14 can then be retracted and absorbable needle 15 clipped off and left in the body to be absorbed, leaving seeds exactly where they were implanted. This embodiment is especially advantageous in that no sterilization of the needle is necessary; it can be sterilized when manufactured and used only once.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. An injector for implanting materials within a body comprising
a unitary elongated needle having a forward sharpened end portion and a rearward end portion, said forward end portion including transverse slots spaced therealong to receive and carry materials to be implanted within a body, means attached to said rearward end portion to rotate said needle radially about its longitudinal axis to expel the materials from said slots into the body; and
an elongated continuous sheath having an open forward end and slidably mounted on and juxtaposed directly surroundingly about said needle over a length at least sufficient to provide a protective cover for all of said slots and any materials therein to be implanted, means for slidingly retracting said sheath on said needle to uncover and expose the entire circumference of said needle and said slots and any materials therein to be implanted on said forward end portion of said needle and to retain said sheath in a retracted position on said needle.

2. The injector of claim 1 wherein said sheath is defined by a cylindrical wall uninterrupted throughout its length.

3. The injector of claim 1 wherein said needle is a cylindrical rod with a multiplicity of slots positioned transversely of said longitudinal axis.

4. The injector of claim 3 wherein said slots are positioned at angle of less than 90° with respect to said longitudinal axis to define shoulders on said cylindrical rod to forcibly eject the implanting materials from said slots upon rotation of said needle at least about 180° after said injector is in said body and said sheath is retracted.

5. The injector of claim 1 wherein said needle is at least twice as long as said sheath.

6. The injector of claim 1 wherein said sheath is generally half as long as said needle.

7. The injector of claim 1 wherein said sheath open forward end and the needle tip of said forward end portion are flush with each other when both are fully extended form a substantially closed and sharpened end adapted to be inserted into a body.

8. The injector of claim 1 wherein said sheath includes a rearward end having a male threaded connection portion, a housing slidably mounted on said needle and having an internal female threaded portion removably coupled to said male threaded connection portion, and clamp means associated with said housing to releasably clamp said needle with respect to said sheath in any selected amount of extension or retraction therebetween.

9. The injector of claim 8 wherein said housing includes a finger grip whereby said housing may be rotated to threadedly couple and uncouple said female threaded portion to and from said male threaded connection.

10. The injector of claim 8 wherein said clamp means is located within said housing.

11. The injector of claim 10 wherein said housing includes an internal tapered cavity and said clamp means includes bifurcated ball sections which coact with said cavity to releasably fix said needle with respect to said sheath and housing.

12. The injector of claim 11 wherein said tapered cavity decreases in the direction opposite to said sheath and towards said means attached to said rearward end portion of said needle.

13. The injector of claim 12 wherein said sheath adjacent said rearward end includes a finger grip.

14. An injector for implanting materials within a body comprising a housing, a slotted needle extensible and retractable from said housing and having slots spaced along the length of the needle to receive materials to be implanted, an uninterrupted sheath around said needle extensible and retractable from said housing separately from said needle, said sheath being shorter in length than said needle so that when retracted on said needle all of said slots are exposed and means to turn said needle radially about its lengthwise axis.

15. The injector of claim 14 for implanting radioactive seeds in animal tissue wherein each of said slots is approximately 0.5 centimeter long and is spaced approximately 1.0 centimeter from the next adjacent slot measured center to center.

16. The injector of claim 15 wherein said needle contains five spaced slots in a needle approximately 5–6 centimeters long.

17. The injector of claim 14 wherein said housing comprises a rigid structure of a forward terminal stop plate and a rearward terminal stop plate joined to each other by at least one guide rod on which is slidably mounted a finger grip rigidly attached to said sheath.

18. The injector of claim 14 wherein said needle comprises a forward slotted portion, a central connecting portion, and a rearward finger grip.

19. The injector of claim 14 wherein said sheath includes a rearward end having a male threaded connection portion, said housing having an internal female threaded portion removably coupled to said male threaded connection portion, and clamp means associated with said housing to releasably clamp said needle with respect to said housing.

20. The injector of claim 19 wherein said clamp means is located within said housing.

21. The injector of claim 20 wherein said tapered cavity decreases in the direction opposite to said sheath and towards said means attached to said rearward end portion of said needle.

22. The injector of claim 19 wherein said housing includes a finger grip whereby said housing may be rotated to threadedly couple and uncouple said female threaded portion to and from said male threaded connection.

23. The injector of claim 22 wherein said housing includes an internal tapered cavity and said clamp means includes bifurcated ball sections which coact with said cavity to releasably fix said needle with respect to said sheath and housing.

24. The injector of claim 23 wherein said sheath adjacent said rearward end includes a finger grip.

25. An injector for implanting radioactive seeds into human tissue comprising a housing, a needle with spaced slots along its length adapted to receive one of said seeds in each slot, said needle being positioned along the lengthwise axis of said housing, and a sheath slidable lengthwise with respect to and surrounding said needle; said sheath being shorter in length than said needle so that when retracted on said needle all of said slots are exposed; said housing including a forward stop plate and a rearward stop plate held in a rigid spaced relationship to each other by two parallel guide rods; said sheath being affixed to a finger grip slidably mounted on said guide rods limited in lengthwise movement by said stop plates; said needle being slidably mounted inside said sheath and capable of being fully extended and capable of being retracted and separated from said sheath; said needle being radially rotatable about the lengthwise axis of said sheath.

26. The injector of claim 25 wherein each of said slots will accomodate a seed approximately 1 millimeter in diameter and 4 millimeters long.

27. The injector of claim 26 wherein said needle contains five slots spaced about 1 centimeter from each other in a center-to-center measurement and each slot being about 0.5 centimeter in length.

28. The injector of claim 25 wherein said needle is a long cylindrical rod and each of said slots is a section cut transversely from said rod with the forward and rearward ends of said slots parallel to each other and angularly disposed to the lengthwise axis of said needle.

29. The injector of claim 25 wherein the tip of said needle and the tip of said sheath when both the needle and the sheath are fully extended form a sharply pointed instrument adapted for injection into a body.

30. The injector of claim 25 wherein the rearward end of said needle is fixed to a transverse plate having a finger grip projecting axially therefrom, said transverse plate having a small projecting knob to fit into a female seat in said rearward stop plate to form an index indicating the rotational position where both said needle and said sheath form a single sharpened injector tip.

31. The injector of claim 25 wherein the tip of said sheath is positioned within said forward stop plate when said finger grip is fully retracted against said rearward stop plate.

* * * * *